(12) United States Patent
Lu et al.

(10) Patent No.: US 11,162,139 B2
(45) Date of Patent: Nov. 2, 2021

(54) METHOD FOR GENOMIC PROFILING OF DNA 5-METHYLCYTOSINE AND 5-HYDROXYMETHYLCYTOSINE

(71) Applicant: SHANGHAI EPICAN GENETECH CO. LTD, Shanghai (CN)

(72) Inventors: Xingyu Lu, Shanghai (CN); Yanqun Song, Shanghai (CN)

(73) Assignee: Shanghai Epican Genetech Co. Ltd., Shanghai (CN)

( * ) Notice: Subject to any disclaimer, the term of this patent is extended or adjusted under 35 U.S.C. 154(b) by 188 days.

(21) Appl. No.: 15/497,247

(22) Filed: Apr. 26, 2017

(65) Prior Publication Data

US 2017/0253924 A1    Sep. 7, 2017

Related U.S. Application Data

(63) Continuation of application No. PCT/CN2016/075863, filed on Mar. 8, 2016.

(30) Foreign Application Priority Data

Mar. 2, 2016 (CN) .......................... 201610119096.2

(51) Int. Cl.
 C12P 19/34 (2006.01)
 C12Q 1/6874 (2018.01)
 C12Q 1/6827 (2018.01)

(52) U.S. Cl.
 CPC ......... *C12Q 1/6874* (2013.01); *C12Q 1/6827* (2013.01)

(58) Field of Classification Search
 USPC ..... 435/6.1, 6.11, 91.1, 91.2, 91.51; 436/94, 436/501; 536/23.1, 24.3, 24.33, 25.3
 See application file for complete search history.

(56) References Cited

U.S. PATENT DOCUMENTS 9,567,633 B2    2/2017  Gao et al.

FOREIGN PATENT DOCUMENTS

| CN | 1463292 A | 12/2003 |
| CN | 103131754 A | 6/2013 |
| CN | 103667442 A | 3/2014 |
| CN | 102971434 B | 4/2014 |
| CN | 104480214 A | 4/2015 |
| WO | WO 2005/121361 | 12/2005 |

OTHER PUBLICATIONS

Zhang et al., Tet-mediated covalent labelling of 5-methylcytosine for its genome-wide detection and sequencing. Nature Communications, 4, 1517, 2013.*
"Site-directed mutagenesis-experimental consideration". Printed on Dec. 2, 2020.*
Yang et al., A simple method for estimating global DNA methylation using bisulfite PCR of repetitive DNA elements. Nucleic Acids Research, 32, e38, 2004.*
Song, et al. "Selective chemical labeling reveals the genome-wide distribution of 5-hydroxymethylcytosine" *Nat. Biotech.* 29(1) (2011) pp. 68-72.
Song, et al. "Sensitive and specific single-molecule sequencing of 5-hydroxymethylcytosine" *Nat. Meth.* 9(1) (2011) pp. 75-77.
Zhao, et al. "DNA Methylation Sequencing Technology" *Acta Chim. Sin. Ch.* 71(1) (2013) pp. 26-35. [Machine Translated].
International Searching Authority. "International Search Report and Written Opinion" PCT/CN2016/075863 (dated Mar. 8, 2016) pp. 1-9.

* cited by examiner

*Primary Examiner* — Frank W Lu
(74) *Attorney, Agent, or Firm* — Dority & Manning, P.A.

(57) ABSTRACT

The present invention provides a method for genomic profiling of DNA 5-methylcytosine and 5-hydroxymethylcytosine, comprising the following steps: (1) DNA purification and fragmentation pretreatment: the target DNA is extracted and then broken to an average of 50 nucleotides to 10,000 nucleotides in length; (2) the repair of trace amount of DNA and the ligation thereof to the adaptor: the pre-treated DNA fragments are repaired and ligated with the sequencing adaptor required for the second-generation sequencing, (3) covalently labeling 5-methylcytosine and 5-hydroxymethylcytosine, (4) solid-phase enrichment of the labeled DNA fragments having cytosine with 5-position modification; (5) the PCR amplification of the solid-phase enriched DNA fragments, the PCR product is obtained and purified to obtain a library for the second-generation sequencing, after mapping the sequencing reads to the genome, the distribution map of the cytosine with 5-position modification in the DNA sample could be generated. The present invention greatly enhances the selectivity and efficiency of binding of the solid-phase surface with the DNA modified base.

15 Claims, 1 Drawing Sheet

Specification includes a Sequence Listing.

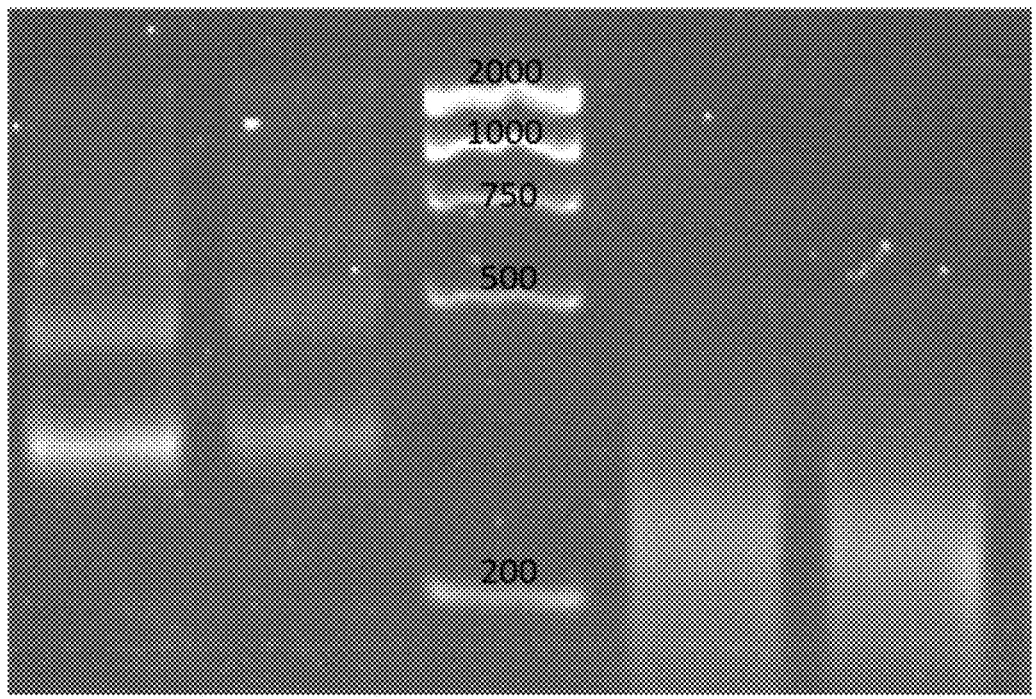

METHOD FOR GENOMIC PROFILING OF DNA 5-METHYLCYTOSINE AND 5-HYDROXYMETHYLCYTOSINE

CROSS-REFERENCE TO RELATED APPLICATIONS

This application is a continuation of International Patent Application No. PCT/CN2016/075863 with a filing date of Mar. 8, 2016, designating the United States, now pending, and further claims priority benefits to Chinese Patent Application No. 2016101190962 filed Mar. 2, 2016. The content of the aforementioned applications, including any intervening amendments thereto, are incorporated herein by reference.

TECHNICAL FIELD

The present invention relates to a method for genomic profiling of DNA 5-methylcytosine and 5-hydroxymethylcytosine, it belongs to the field of DNA sequencing.

BACKGROUND OF THE PRESENT INVENTION

DNA is not only composed of four bases cytosine, thymine, guanine and adenine 5-methylcytosine and 5-hydroxymethylcytosine are important modifications in DNA, they are the fifth and sixth bases on DNA. They are important markers for regulating biological pathways, cell lifecycles, and play multiple biological functions, including transcriptional regulation, transposon silencing, gene imprinting and X chromosome inactivation. In a variety of diseases, especially cancer and other major diseases, 5-methylcytosine and 5-hydroxyethylcytosine display specific genome distributions. In the early stages of fertilization and embryonic development, they show significant changes in distribution, and are considered to be markers of these processes. Therefore, it is very important to use the sequencing techniques to fully understand the process.

Because of the physical and chemical properties of the cytosines with 5-position modification are similar, they cannot be distinguished directly with the existing first generation or second generation sequencing technology. A common method is to break up the DNA into fragments and then specifically bind the cytosine with 5-position modification to specifically enrich the DNA fragment containing the cytosine with 5-position modification. The distribution, information of cytosines with 5-position modification in the genome can be obtained by sequencing the enriched fragments, and various qualitative, semi-quantitative, quantitative bioinformatics analyses can be carried out using this information.

The advantage of this method is that the sequencing depth is low, the cost is low, and the coverage is good. There are two types of enrichment means commonly used, one is specific antibody capture, and the other is specific chemical biological marker capture. Both of these methods can provide good reproducible results. For the enrichment mean of antibody capture, the antibody is more expensive, the sequence requirements for the captured site are higher, and binding property of sequences with sparsely distributed modifications is poor, therefore, error may be introduced. And the specific chemical biological marker capture may introduce backgrounds because the selectivity of chemical bioreactions is not completely optimized, which lead to off-target by-products. Because of the enrichment process, a large number of DNA fragments free of 5-position modified cytosines are discarded in the process, leading to the need for large amounts of DNA as starting material in sequencing applications. This type of conventional sequencing method generally takes only more than 1 micrograms of DNA as the starting sample size for sequencing. In actual biological, medical applications, often only 1 micrograms or less, even 1-10 nanograms of DNA samples are obtained, the detection method of such samples will directly obtain gene regulation information with biological and clinical values, and thus is of great significance in the biological and clinical research and development and testing.

According to the above analysis, the existing enrichment means do not have a major breakthrough for three reasons: firstly, the amount of enriched DNA is too small, and loss in the sequencing library construction is too great. The traditional, process of establishing a library involves multi-step reaction and purification, and the purification efficiency of a small amount of DNA is low; secondly, the enrichment method has reduced efficiency on the low concentration of DNA, when using antibody enrichment, the binding efficiency directly relates to the antigen concentration, the reported antigen-antibody binding capacity cannot meet the need of reaction at very low DNA concentration: thirdly, the enriched DNA cannot be effectively eluted from the solid phase, DNA eluted from the solid, phase, in the enrichment process is only less than 5% of the original DNA. The purification or chemical reactions involved in the elution process will cause great loss of the captured DNA fragments, resulting in fail of subsequent PCR reactions or introducing a large number of sequencing errors.

SUMMARY OF PRESENT INVENTION

It is an object of the present invention to provide a method for genomic profiling of DNA 5-methylcytosine and 5-hydroxymethylcytosine to improve the sequencing efficiency of cytosines with 5-position modification.

The present invention uses the following technical solutions:

a method for genomic profiling of DNA 5-methylcytosine and 5-hydroxymethylcytosine, comprising the steps of:

(1)DNA purification and fragmentation pretreatment:

The target DNA is extracted and then using a mechanical force or digestive enzyme to break it to an average of 50 nucleotides to 10,000 nucleotides in length;

(2) The repair of trace amount of DNA and the ligation thereof to the adaptor:

The pre-treated DNA fragments, are repaired and ligated with the sequencing adaptor, required for the second-generation sequencing;

(3) Covalent labeling of 5-methylcytosine with 5-hydroxymethylcytosine; Cytosine with 5-position modification in the DNA fragment to which the adaptor is ligated is covalently labeled;

(4) Solid-phase enrichment of the labeled DNA fragment having cytosine with 5-position modification:

The DNA fragment of labeled cytosine with 5-position modification is bound to the solid phase in the binding buffer, and the solid phase surface is repeatedly washed to remove the unbound DNA fragment:

(5) the PCR amplification primers corresponding to the adaptor are used to carry out an amplification of the solid-phase enriched DNA fragments.

The PCR product is obtained and purified to obtain a library for the second-generation sequencing. After mapping the sequencing reads to the genome, the distribution map of the cytosine with 5-position modification in the DNA sample could be generated.

Further, the method for genomic profiling of DNA 5-methylcytosine and 5-hydroxymethylcytosine according to the present invention may further have the following feature that in step (1), the DNA fragment is derived from free DNA fragments in a body fluid; or genomic DNA purified from tissues, cells and organelles.

Further, the method for genomic profiling of DNA 5-methylcytosine and 5-hydroxymethylcytosine according to the present invention may further have the following feature that in step (1), the body fluid of the DNA fragment is derived from blood, urine, sweat, sputum, feces, cerebrospinal fluid, ascites, pleural effusion, bile, pancreatic fluid or other body fluids.

Further, the method for genomic profiling of DNA 5-methylcytosine and 5-hydroxymethylcytosine according to the present invention may have the following feature that the DNA fragment repair in the step (2) is a step of repairing base damage in DNA fragment, and 5' and 3' of DNA are made up to a blunt-end.

Further, the method, for genomic profiling of DNA 5-methylcytosine and 5-hydroxymethylcytosine according to the present invention may further have the following feature that in step (3), the method of labeling comprises the steps of: i) an azide-group modified sugar is covalently linked to the hydroxymethyl group of 5-hydroxymethylcytosine using transglycosidase, ii) azido-sugar modified 5-hydroxymethylcytosine reacts with click-chemistry substrate linked directly or indirectly to a biotin.

Further, the method for genomic profiling of DNA 5-methylcytosine and 5-hydroxymethylcytosine according to the present invention may also have the following feature that the Transglycosylase includes, but is not limited to, T4 bacteriophage enzyme β-glucosyltransferase, T4 bacteriophage enzyme α-glucosyltransferase and its derivatives, analogs, or recombinant enzymes; azide-group modified sugars include, but not limited to, 6-N3-glucose or other azido-modified sugar.

Further, the method for genomic profiling of DNA 5-methylcytosine and 5-hydroxymethylcytosine according to the present invention may further have the following feature that labeling methylcytosine includes the steps of i) 5-methylcytosine is oxidized to 5-hydroxymethylcytosine using murine Tet oxidase or a derivative thereof, analogues, recombinant enzymes, ii) biotin labeling of 5-hydroxymethylcytosine is carried out as described above.

Further, the method for genomic profiling of DNA 5-methylcytosine and 5-hydroxymethylcytosine according to the present invention may further have the following feature that labeling steps of 5-hydroxymethylcytosine and 5-methyleytosine can be carried out in sequence or simultaneously in a reaction.

Further, the DNA 5-methylcytosine and the 5-hydroxymethylcytosine genome sequencing according to the present invention may further have the following feature that in step (4), the solid phase material includes a magnetic ball having a diameter of 1 nm to 100 μm, agarose beads of 1 nm to 100 μm in diameter, artificial macromolecule balls with diameters of 1 nm to 100 μm, silicon wafers with surface modification or other biochips.

Further, the method for genomic profiling of DNA 5-methylcytosine and 5-hydroxymethylcytosine according to the present invention may further have the following feature that in step (5),the qualified sequencing library is obtained by amplification of 1-40 PCR cycles on the solid phase directly, or after the amplification by 1-40 PCR cycles the solid-liquid phase is separated and then the qualified sequencing library is obtained by further amplification of 1 to 40 PCR cycles.

In the above step (1), the body fluid source of the DNA fragment is derived from, but not limited to, a human body fluid such as blood, urine, sweat, sputum, feces, cerebrospinal fluid, ascites, pleural effusion, bile, pancreatic fluid and the like.

In the above step (1), the tissue, cell and organelle are derived from, but not limited to, for example, the living tissue, the cultured cells, the shedding cells, the blood circulation cells, the cells washed during surgeries, and the like.

In the above step (1), the method of extracting a DNA fragment or a complete genomic DNA includes a conventional purification method or a commercial purification kit. The method includes, but is not limited to, one of the techniques or a combination of several of the techniques such as chloroform-phenol extraction, proteinase K digestion, silica-gel membrane spin column, magnetic bead, ethanol, isopropanol precipitatior. Purification kits include, but are not limited to, QIAamp fast DNA tissue kit (Qiagen), ZR Genomic DNA-Tissue Kits (Zymo).

In the above step (1), mechanical forces include, but are not limited to, techniques such as severe shocks and ultrasonic methods. Digestive enzymes include, but are not limited to, NEBNext dsDNA Fragmentase (NEB).

The DNA fragment repair in the above step (2) refers to repairing the base damage in the DNA fragment and making up the 5' and 3' of the DNA double strand into a blunt end. The method of ligating DNA fragments to sequencing adaptor includes, but is not limited to: i) blunt-end ligation; ii) one to more dA are added at, the end of the 3' end of the DNA fragment, using the corresponding dT in the adaptor to carry out the ligation. The enzymes involved in repairing and ligating include, but are not limited to, one or a combination of T4 polymerase, T4 Kinase, Klenow exo-. Repairing and ligation can also use commercially available kits, including but not limited to TruSeq Nano DNA Library Prep Kit (Illumina), Kapa Hyper Prep Kit (Kapa), NEBNext® DNA Library Prep Master Mix Set (NEB).

In the above step (3), the chemical biological labeling method used means that labeling 5-hydroxymethylcytosine includes the steps of i) an azide-group modified sugar is covalently linked to the hydroxymethyl group of 5-hydroxymethylcytosine using transglycosidase, see the following reaction formula, the substrate is UDP-6-N3-Glucose.

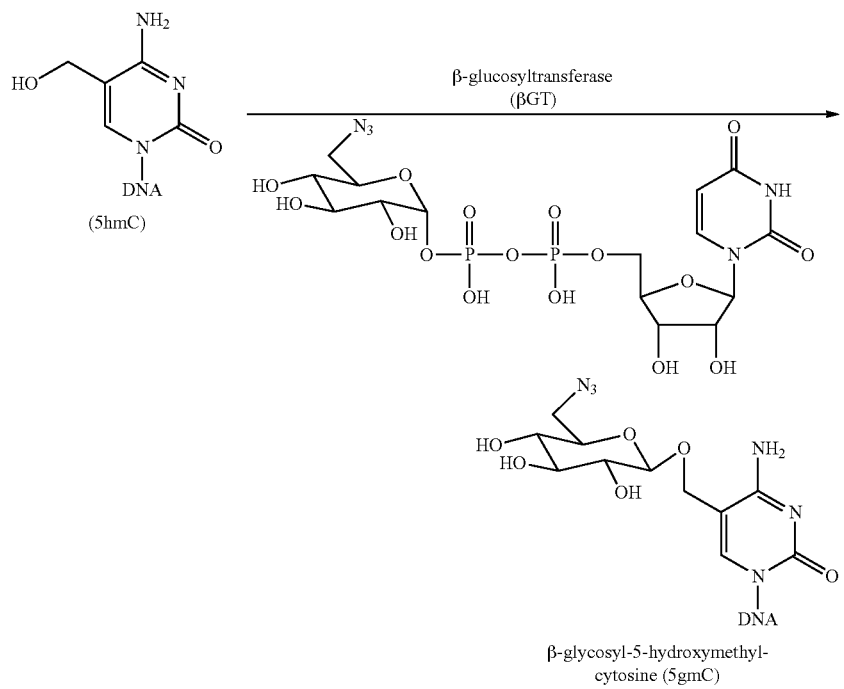

β-glycosyl-5-hydroxymethyl-
cytosine (5gmC)

5-hydroxymethylcytosine covalent labeling reaction

Transglycosylase includes, but is not limited to, T4 bacteriophage enzyme βglucosyltransferase, T4 bacteriophage enzyme α-glucosyltransferase and its derivatives, analogs, or recombinant enzymes. Azide-group modified sugars include, but are, not limited to, 6-N3-glucose or other chemical modified sugars including, but not limited to, carbonyl, mercapto, hydroxy, carboxy, carbon-carbon double bonds, carbon-carbon triple bonds, disulfide bonds, amide group, diene, ii) click-chemistry substrate or a corresponding chemical reaction substrate linked directly or indirectly with biotin reacts with 5-hydroxymethylcytosine modified with azido-sugar or other chemical groups.

The reaction groups include but not limited to the following compounds containing triple bonds:

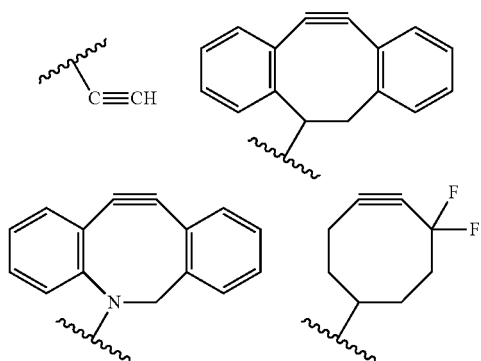

The chemical groups and reactions that indirectly bind to biotin include, but are not limited to, carbonyl, mercapto, hydroxy, carboxy, carbon-carbon double bonds, carbon-carbon triple bonds, disulfide bonds, amine groups, amide, groups, diene.

Labeling methylcytosine includes the step of: i) the sugar, which is not modified with the modifying group in the next reaction, is covalently linked to the hydroxymethyl group of 5-hydroxymethylcytosine using transglycosylase, for masking a low content of 5-hydroxymethylcytosine relative to 5-methylcytosine; ii) 5-methylcytosine is oxidized by ten-eleven translocation (TET) oxidase or its derivatives, analogues and recombinase.

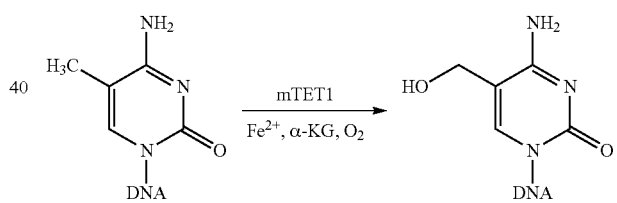

Oxidation Action of 5-methylcytosine 5-methylcytosine is oxidized to 5-hydroxymethylcytosine (see, reaction formula of oxidation reaction of 5-methylcytosine), as mentioned above, the 5-hydroxymethylcytosine is labeled with biotin.

The labeling step of the above 5-hydroxymethylcytosine and 5-methylcytosine can also be carried out in sequence or simultaneously in one reaction.

In the above step (4), the solid phase used is a solid phase which is directly supported with avidin or indirectly supported by a chemical biology method with avidin, the solid phase material includes but not limited to, a magnetic pellet having a diameter of 1 nm to 100 μm, an agarose pellet having a diameter of 1 nm to 100 μm, an artificial macromolecule pellet having a diameter of 1 nm to 100 μm, a surface-modified silicon wafer or other biochip.

In the above step (4), the binding liquid and washing liquid used include a buffer such as Tris-HCl, MOPS, HEPES (pH=6.0 to 10.0, at a concentration of 1 mM to 1M); NaCl (0-2M); surfactants such as Tween20 (0.01%-5%).

In the above step (5), the amplification is carded out on the solid phase, which can be one of the following processes i) a qualified sequencing library is obtained by an amplification of 1-40 PCR cycles directly on the solid phase, ii) after the amplification by 1-40 PCR cycles the solid-liquid phase is separated, then amplification is further performed by 1-40 PCR cycles to obtain a qualified sequencing library, iii) The DNA fragment is eluted from solid phase elution followed by amplification of 40 PCR cycles to obtain a qualified sequencing library.

In the above steps (1) to (5), the nucleic acid purification step after each reaction may be carried out using a conventional purification method or a commercial purification kit. The method includes, but not limited to, one of the techniques or a combination of several of the techniques of silica gel membrane spin column, magnetic bead, ethanol, isopropanol precipitation and the like. Purification kits include but are not limited to: AmpureXP beads, Minelute PCR purification Kit (Qiagen), DNA Clean & Concentrator (Zymo).

Compared with the prior art, the method for genomic profiling of DNA 5-methyicytosine and 5-hydroxymethylcytosine according to the present invention greatly enhance the selectivity and efficiency of binding between the solid phase surface and the modified DNA base due to application of trace cell-free DNA second-generation sequencing technology and effective chemical biology orthogonal reaction. In the order of 1-100 ng DNA, the binding efficiency of conventional antigen-antibody responses cannot provide sufficient selectivity so that the relevant application can only be used in large amounts of DNA samples derived from cultured cells or tissues.

The present invention further greatly improves the efficiency of enrichment by using a high salt and a surfactant to further wash away DNA fragments without modified base, by using a high binding ability of biotin and avidin on the basis of covalent linkage.

DESCRIPTION OF THE DRAWINGS

FIG. 1 is an electrophoresis image of the final constructed libraries in Examples 1-4.

DETAILED DESCRIPTION OF PREFERRED EMBODIMENTS

Hereinafter, specific embodiments of the present invention will be described with reference to specific embodiments.

EXAMPLE 1

Construction of 5-methylcytosine Sequencing Library from Plasma, Cell-Free DNA (1)DNA purification and fragmentation pretreatment:

4 mL human blood is taken with EDTA anticoagulant tube, and stored at 4 degrees Celsius. Within 6 hours, it is centrifuged for 10 min with a speed of 2000 g; then centrifuged for 10 min with a speed of 13000 g. Plasma is obtained and cell-free DNA is extracted.

(2) The trace amount of DNA is repaired and ligated with the adaptor, and the adaptor having a sequence as follows:

(SEQ ID NO: 1)
5'-p-GATCGGAAGAGCACACGTCTGAACTCCAGTCACAAACATCGATC

TCGTATGCCGTCTTCTGCTTG-3';

(SEQ ID NO: 2)
5'-AATGATACGGCGACCACCGAGATCTACACATGCCTAAACACTCTTT

CCCTACACGACGCTCTTCCGATC*T-3',
* represents thio.

0.5-10 ng of cell-free DNA is repaired and ligated with the sequencing adaptor required for secondary sequencing. DNA fragment repair refers to repairing base damage in DNA fragments and making up 5' and 3' of DNA to a blunt-end. The steps are as follows:

1. 50 uL DNA is subjected to the End Repair & A-Tailing reaction in the PCR tube according to the Kapa Hyper Pero Kit specification.

| Reactants | Volume (uL) |
| --- | --- |
| Free DNA | 50 |
| End Repair & A-Tailing Buffer | 7 |
| End Repair & A-Tailing Enzyme mix | 3 |

2. Reaction is heated according to the PCR procedures

| Step | Temperature | Time |
| --- | --- | --- |
| End Repair & A-Tailing | 20 | 30 min |
|  | 65 | 30 min |

3. The following reaction mixture is configured in a 1.5 mL low adsorption EP tube:

| Reactants | Volume (uL) |
| --- | --- |
| Nuclease free water | 5 |
| Ligation Buffer | 30 |
| DNA Ligase | 10 |

4. Adding the following reactants:

| Reactants | Volume (uL) |
| --- | --- |
| Mixture of ligation reaction | 35 |
| Adaptor | 5 |

5. Reaction is heated according to the following PCR procedures:

| Step | Temperature | Time |
| --- | --- | --- |
| Adaptor Ligation | 20 | 20-300 min |

6. The reaction is purified using AmpureXP beads and eluted with 20 uL of a buffer containing Tris-HCl (10 mM, pH=8.0) and EDTA (0.1).

(3) covalently labeling 5-methylcytosine:

The 5-position modified cytosine in the DNA fragment to which the adaptor is ligated is covalently labeled; the naturally occurring 5-hydroxymethylcytosine is masked with a sugar free of modifying group of labeling reaction, and methylcytosine is oxidized to 5-hydroxymethylcytosine by mouse TET oxidase and 5-hydroxymethylcytosine is labeled with biotin.

1. Labeling reaction is configured using the above purified DNA solution:

| Reactants | Final concentration |
| --- | --- |
| UDP -Glu | 50 uM |
| βGT | 1 uM |
| Mg2+ | 25 mM |
| HEPES pH = 8.0 | 50 mM |
| DNA (20 uL) | |

The above reactants are added to the DNA solution. Reaction is performed for 1 hour at 37 degrees Celsius in the water bath. The reactants are taken, and purified with AmpureXP beads.

2. Tet oxidation and azide labeling reaction

| Reactants | Final concentration |
| --- | --- |
| UDP-N3-Glu | 50 uM |
| βGT | 1 uM |
| mTet1 | 3 uM |
| Mg2+ | 10 mM |
| HEPES pH = 8.0 | 50 mM |
| Fe2+ | 75 uM |
| Ascorbic Acid | 2 mM |
| Dithiothreitol | 1 mM |
| DNA (20 uL) | |

Reaction is performed for 1 hour at 37 degrees Celsius. Purification is made with AmpureXP beads.

3. Adding triple bond compound

| Reactants | Final concentration |
| --- | --- |
| DBCO-Biotin | 2 mM |
| DNA (20 uL) | |

Reaction is performed for 2 hours at 37 degrees Celsius. Purification is made with AmpureXP beads.

(4) DNA fragment containing labeled 5-methylcytosine is enriched with solid phase:

1. 0.5 uL C1 streptadvin beads (life technology) is vortexed and mixed for 30 seconds.
2. Magnetic beads are washed three times with 100 uL wash liquid (5 mM Tris, pH=7.5, 1M NaCl, 0.02% Tween20).
3. The binding buffer solution (10 mM Tris, pH=7.5, 2M NaCl, 0.04% Tween20 or other surfactants) is added in equal volume as DNA solution to magnetic beads, it is pipetted uniformly with pipette. The mixed liquid of magnetic beads is added into purified labeled hmC DNA solution, mixed on the rotary mixer for 15 min.
4. The magnetic beads are washed three times with 100 uL washing liquid (5 mM Tris, pH=7.5, 1M NaCl, 0.02% Tween20).

(5) PCR AMPLIFICATION AND PURIFICATION

1. PCR reaction is performed as follows:

| Reactants | Volume (uL) |
| --- | --- |
| 2XPCR master mix | 25 |
| PCR primer | 1.25 |

2. The circulation temperatures of reaction are as follows:

| Step | Temperature | Time | Cycle number |
| --- | --- | --- | --- |
| 1 | 98 | 45 seconds | 1 |
| 2 | 98 | 15 seconds | 10-14 |
| 3 | 60 | 30 seconds | |
| 4 | 72 | 30 seconds | |
| 5 | 72 | 1 minute | 1 |
| 6 | 4 | ∞ | 1 |

AmpureXP beads are purified and final sequencing library is obtained (see FIG. 1).

EXAMPLE 2

Construction of Hydroxymethylcytosine Sequencing Library from Plasma Cell-Free DNA (1) DNA purification and fragmentation pretreatment:

4 mL human blood is taken with EDTA anticoagulant tube, and stored at 4 degrees Celsius. In 6 hours, it is centrifuged for 10 min with a speed of 2000 g, and then centrifuged for 10 min with a speed of 13000 g. Plasma is obtained and cell-free DNA is extracted.

(2) Repairing of trace amount of DNA and ligation of adaptor:

0.5-10 ng of free DNA is repaired and ligated with the sequencing adaptors required for secondary sequencing. DNA fragment repair refers to repairing base damage in DNA fragments and making up 5' and 3' of DNA into a blunt end. Steps are as follows:

1. 50 uL DNA is added to End Repair & A-Tailing reaction in PCR tube according to the specification of Kapa Hyper Perp Kit.

| Reactants | Volume (uL) |
| --- | --- |
| Free DNA | 50 |
| End Repair & A-Tailing Buffer | 7 |
| End Repair & A-Tailing Enzyme mix | 3 |

2. Reaction is heated by the following PCR procedure:

| Step | Temperature | Time |
| --- | --- | --- |
| End Repair & A-Tailing | 20 | 30 min |
| | 65 | 30 min |

3. The following ligation reaction mixture is configured in a 1.5 mL low adsorption EP tube:

| Reactants | Volume (uL) |
| --- | --- |
| Nuclease free water | 5 |
| Ligation Buffer | 30 |
| DNA Ligase | 10 |

4. Adding the following reactants:

| Reactants | Volume (uL) |
| --- | --- |
| Mixture of ligation reaction | 35 |
| Adaptor | 5 |

5. Reaction is heated according to the following PCR procedure

| Step | Temperature | Time |
| --- | --- | --- |
| Adaptor Ligation | 20 | 20 Min |

6. The reaction is purified using AmpureXP beads and eluted with 20 uL of a buffer containing Tris-HCl (10 mM, pH 8.0) and EDTA (0.1 mM).

(3) Covalently labeling 5-hydroxymethylcytosine:

| Reactants | Final concentration |
| --- | --- |
| UDP -NS-Glu | 50 uM |
| βGT | 1 uM |
| Mg2+ | 25 mM |
| HEPES pH = 8.0 | 50 mM |
| DNA (20 uL) | |

Reaction is performed for 1 hour at 37 degrees Celsius. Purifications made with AmpureXP beads.

Adding triple bond compound

| Reactants | Final concentration |
| --- | --- |
| DBCO-Biotin | 2 mM |
| DNA (20 uL) | |

Reaction is performed for 2 hours at 37 degrees Celsius. Purification made with AmpureXP beads.

(4) DNA fragment containing labeled 5-position modified cytosine is enriched with solid phase:

1. 0.5 uL, C1 streptadvin beads (life technology) are vortexed and mixed for 30 seconds, 2. Magnetic beads are washed three times with 100 uL wash liquid (5 mM Tris, pH=7.5, 1M NaCl, 0.02% Tween20).

3. The binding buffer solution (10 mM Tris, pH=7.5, 2M NaCl, 0.04% Tween20 or other surfacants) is added in equal volume as DNA solution to magnetic beads, it is pipetted uniformly with pipette. The mixed liquid of magnetic beads is added into purified labeled hmC DNA solution, mixed on the rotary mixer for 15 min.

4. The magnetic beads are washed three times With 100 uL washing liquid (5 mM Tris, pH=7.5, 1M NaCl, 0.02% Tween20).

(5) PCR amplification and purification
1. PCR reaction is performed as follows:

| Reactants | Volume (uL) |
| --- | --- |
| 2XPCR master mix | 25 |
| PCR primer | 1.25 |

2. Temperatures of reaction cycles are as follows:

| Step | Temperature | Time | Cycle number |
| --- | --- | --- | --- |
| 1 | 98 | 45 seconds | 1 |
| 2 | 98 | 15 seconds | 14-18 |
| 3 | 60 | 30 seconds | |
| 4 | 72 | 30 seconds | |
| 5 | 72 | 1 minute | 1 |
| 6 | 4 | ∞ | 1 |

AmpureXP beads are used for purification, and sequencing library is obtained, see FIG. 1.

EXAMPLE 3

Construction of 5-methylcytosine Sequencing Library is Obtained from Tissue DNA (1) Extraction and fragmentation pretreatment of DNA Tissue genome DNA is extracted with ZR Genomic DNA-Tiss Kits (Zymo). 0.5-100 ng genome DNA is subjected to the reaction according to Kapa HyperPlus Library Preparation Kit so as to break up the genome DNA.

| Reactants | Volume (uL) |
| --- | --- |
| Genome DNA | 35 |
| Kapa Frag Buffer (10X) | 5 |
| Kapa Frag Enzyme | 10 |

(2) Repairing of trace amount of DNA and ligation of adaptor:

The fragmented DNA is repaired and ligated with the adaptors required for the second-order sequencing. DNA fragment repair refers to repairing base damage in DNA fragments and filling 5' and 3' of DNA into fiat ends. Steps are as follows:

1. 50 uL DNA is subjected to the End Repair & A-Tailing reaction in the PCR tube according to the Kapa HyperPlus Library Preparation Kit specification.

| Reactants | Volume (uL) |
| --- | --- |
| Fragmented DNA | 50 |
| End Repair & A-Tailing Buffer | 7 |
| End Repair & A-Tailing Enzyme mix | 3 |

2. Reaction is heated according to the following PCR procedures:

| Step | Temperature | Time |
| --- | --- | --- |
| End Repair & | 20 | 30 min |
| A-Tailing | 65 | 30 min |

3. The following ligation reaction mixture is configured in a 1.5 mL low adsorption EP tube:

| Reactants | Volume (uL) |
| --- | --- |
| Nuclease free water | 5 |
| Ligation Buffer | 30 |
| DNA Ligase | 10 |

4. Adding the following reactants:

| Reactants | Volume (uL) |
| --- | --- |
| Mixture of ligation reaction | 35 |
| Adaptor | 5 |

5. Reaction is heated according to the following PCR procedures:

| Step | Temperature | Time |
| --- | --- | --- |
| Adaptor Ligation | 20 | 20-300 min |

6. The reaction is purified using AmpureXP beads and eluted with 20 uL of a buffer containing Tris-HCl (10 mM, pH=8.0) and EDTA (0.1).

(3) Covalently labeling 5-hydroxymethylcytosine:

The 5-position modified cytosine in the DNA fragment to which the adaptor is ligated is covalently labeled; the naturally occurring 5-hydroxymethylcytosine is masked with a sugar free of modifying group in labeling reaction, and methylcytosine is oxidized to 5-hydroxymethylcytosine by mouse TET oxidase and 5-hydroxymethylcytosine is labeled with biotin.

1. Labeling reaction is configured following the above puffed DNA solution

| Reactants | Final concentration |
| --- | --- |
| UDP-Glu | 50 uM |
| βGT | 1 uM |
| Mg2+ | 25 mM |
| HEPES pH = 8.0 | 50 mM |
| DNA (20 uL) | |

Adding the above to DNA solution, reaction is performed at 37 degrees Celsius in water bath. Reactants are taken, and purification is made with AmpureXP beads.

2. Tet oxidation and azide-sugar labeling reaction:

| Reactants | Final concentration |
| --- | --- |
| UDP-N3-Glu | 50 uM |
| βGT | 1 uM |
| mTet1 | 3u M |
| Mg2+ | 10 mM |
| HEPES pH = 8.0 | 50 mM |
| Fe2+ | 75 uM |
| Ascorbic Acid | 2 mM |
| Dithiothreitol | 1 mM |
| DNA (20 uL) | |

Reaction is performed for 1 hour at 37 degrees Celsius. Purification is made with AmpureXP beads.

3. Adding triple bond compound

| Reactants | Final concentration |
| --- | --- |
| DBCO-Biotin | 2 mM |
| DNA (20 uL) | |

Reaction is performed for 2 hours at 37 degrees Celsius. Purification is made with AmpureXP beads.

(4) DNA fragment containing labeled 5-methylcytosine is enriched with solid phase:

1. 0.5 uL C1 streptadvin beads life technology) are vortexed and mixed for 30 seconds.

2. Magnetic beads are washed three times with 100 uL wash liquid (5 mM Tris, pH=7.5, 1M NaCl, 0.02% Tween20).

3. The binding buffer solution (10 M Tris, pH=7.5, 2M NaCl, 0.04% Tween20 or other surfactants) is added in equal volume as DNA solution to magnetic beads, it is pipetted uniformly with pipette. The mixed liquid of magnetic beads is added into purified labeled hmC DNA solution, mixed on the rotary mixer for 15 min.

4. Magnetic beads are washed three times 100 uL wash liquid 5 mM Tris, pH=7.5 1M NaCl, 0.02% Tween20).

(5) PCR amplification and purification

1. PCR reaction performed as the following:

| Reactants | Volume (uL) |
| --- | --- |
| 2XPCR master mix | 25 |
| PCR primer | 1.25 |

2. Temperatures of reaction cycles are as follows:

| Step | Temperature | Time | Cycle number |
| --- | --- | --- | --- |
| 1 | 98 | 45 seconds | 1 |
| 2 | 98 | 15 seconds | 10-14 |
| 3 | 60 | 30 seconds | |
| 4 | 72 | 30 seconds | |
| 5 | 72 | 1 minute | 1 |
| 6 | 4 | ∞ | 1 |

AmpureX P beads are used for purification, and fine sequencing library is obtained, see FIG. 1.

EXAMPLE 4

Construction of-5-hydroxymethyleytosine Sequencing Library from Tissue DNA (1) DNA purification and fragmentation pretreatment:

Tissue genome DNA is extracted with ZR Genomic DNA-Tissue Kits (Zymo). 0.5-100 ng genome DNA is subjected to the reaction according to Kapa HyperPlus Library Preparation Kit so as to break up the genome DNA.

| Reactants | Volume (uL) |
| --- | --- |
| Genome DNA | 35 |
| Kapa Frag Buffer (10X) | 5 |
| Kapa Frag Enzyme | 10 |

(2) Repairing of trace amount of DNA and ligation of adaptor:

The fragmented DNA is repaired and ligated with the adaptors required for the second-order sequencing, DNA fragment repair refers to repairing base damage in DNA fragments and making up 5' and 3' of DNA into a brunt-end. Steps are as follows:

1. 50 uL DNA is subjected to the End Repair & A-Tailing reaction in the PCR tube according to the Kapa HyperPlus Library Preparation Kit specification.

| Reactants | Volume (uL) |
| --- | --- |
| cfDNA | 50 |
| End Repair & A-Tailing Buffer | 7 |
| End Repair & A-Tailing Enzyme mix | 3 |

2. Reaction is heated according to the following PCR procedures:

| Step | Temperature | Time |
| --- | --- | --- |
| End Repair & A-Tailing | 20<br>65 | 30 min<br>30 min |

3. The following ligation reaction mixture is configured in a 1.5 mL, low adsorption EP tube:

| Reactants | Volume (uL) |
| --- | --- |
| Nuclease free water | 5 |
| Ligation Buffer | 30 |
| DNA Ligase | 10 |

4. Adding the following reactants:

| Reactants | Volume (uL) |
| --- | --- |
| Mixture of ligation reaction | 35 |
| Adaptor | 5 |

5. Reaction is heated according to the following PCR procedures:

| Step | Temperature | Time |
| --- | --- | --- |
| Adaptor Ligation | 20 | 20 min |

6. The reaction is purified using AmpureXP beads and eluted with 20 uL of a buffer containing Tris-HCl (10 mM, pH=8.0) and EDTA (0.1 mM).

(3) Covalently labeling 5-hydroxymethylcytosine:

1. The following reaction is performed on purification product

| Reactants | Final concentration |
| --- | --- |
| UDP-N3-Glu | 50 uM |
| βGT | 1 uM |
| Mg2+ | 25 mM |
| HEPES pH = 8.0 | 50 mM |
| DNA (20 uL) | |

Reaction is performed for 1 hour at 37 degrees Celsius. Purification is made with AmpureXP beads.

2. Adding triple bond compound

| Reactants | Final concentration |
| --- | --- |
| DBCO-Biotin | 2 mM |
| DNA (20 uL) | |

Reaction is performed for 2 hours at 37 degrees Celsius, Purification is made with AmpureXP beads.

(4) DNA fragment containing labeled 5-position modified methylcytosine is enriched with solid phase:

1. 0.5 uL C1 streptadvin beads (life technology) are vortexed and mixed for 30 seconds.

2. Magnetic beads are washed three times with 100 uL wash liquid (5 mM Tris, pH=7.5, 1M NaCl, 0.02% Tween20).

3. The binding buffer solution (10 mM Tris, PH=7.5, 2M NaCl, 0.04% Tween20 or other surfactants) is added in equal volume as DNA solution to magnetic beads, it is pipetted uniformly with pipette. The mixed liquid of magnetic beads is added into purified labeled hmC DNA solution, mixed on the rotary mixer for 15 min.

4. Magnetic beads are washed three times with 100 uL wash liquid (5 mM Tris, 7.5, 1M NaCl, 0.02% Tween20).

(5) PCR amplification and purification

1. PCR reaction is performed according to the following,

| Reactants | Volume (uL) |
| --- | --- |
| 2XPCR master mix | 25 |
| PCR primer | 1.25 |

2. Temperature of reaction cycles are as visits:

| Step | Temperature | Time | Cycle number |
| --- | --- | --- | --- |
| 1 | 98 | 45 seconds | 1 |
| 2 | 98 | 15 seconds | 14-18 |
| 3 | 60 | 30 seconds | |
| 4 | 72 | 30 seconds | |
| 5 | 72 | 1 minute | 1 |
| 6 | 4 | ∞ | 1 |

AmpureXP beads are used for purification, and final sequencing library is obtained, see FIG. 1.

We claim:

1. A method for genetic mapping 5-hydroxymethylcytosines in a target DNA, comprising the following steps:
   (1) pretreating the target DNA by extracting the target DNA and then, using a mechanical force or a digestive enzyme, breaking the target DNA to DNA fragments having an average of 50 nucleotides to 10,000 nucleotides in length;
   (2) repairing the DNA fragments and ligating the DNA fragments to a sequencing adaptor required for next generation sequencing;
   (3) covalently labeling 5-hydroxymethylcytosines in the DNA fragments to which the adaptor is ligated, said labeling comprising the steps of: i) covalently linking an azido-group modified sugar to a hydroxymethyl group of the 5-hydroxymethylcytosines by use of a glucosyltransferase and thereby producing an azido sugar-modified 5-hydroxymethylcytosine; and ii) reacting the azido sugar-modified 5-hydroxymethylcytosine with a click-chemistry to a substrate directly or indirectly linked to a biotin, thereby obtaining a labeled 5-hydroxymethylcytosine in the DNA fragments;
   (4) enriching the DNA fragments having labeled 5-hydroxymethylcytosines on a solid phase by binding the DNA fragments having labeled 5-hydroxymethylcytosines to the solid phase in a binding buffer, and repeatedly washing a surface of the solid phase to remove DNA fragments that are not bound to the solid phase; and
   (5) hybridizing PCR amplification primers to the sequencing adaptor to carry out a PCR amplification of the DNA fragments having labeled 5-hydroxymethylcytosines enriched on the solid phase to obtain a PCR product, and further purifying the PCR product to obtain a sequencing library for the next generation sequencing, and generating a distribution map after the next generation sequencing and mapping sequencing reads of the purified PCR product to a genome of the target DNA.

2. The method according to claim 1,
   wherein in step (1), the target DNA are derived from free DNA fragments in a body fluid, or from genomic DNA purified from tissues, cells, or organelles.

3. The method according to claim 2,
   wherein the body fluid is derived from blood, urine, sweat, sputum, cerebrospinal fluid, ascites, pleural effusion, bile, or pancreatic fluid.

4. The method according to claim 1,
   wherein said repairing the DNA fragments in the step (2) comprises repairing base damage in the DNA fragments, and making the 5' and 3' of the DNA fragments to blunt-ends.

5. The method according to claim 1,
   wherein the glucosyltransferase includes, but is not limited to, β-glucosyltransferase, α-glucosyltransferase and its derivatives, analogs or recombinant enzymes; and the azido group modified sugar includes, but is not limited to, 6-N3-glucose or another azido-modified sugar.

6. The method according to claim 1,
   wherein in step (4), the solid phase comprises a magnetic ball having a diameter of 1 nm to 100 μm, agarose beads having a diameter of 1 nm to 100 μm, artificial macromolecule balls having a diameter of 1 nm to 100 μm, silicon wafers with surface modification, or biochips.

7. The method according to claim 1,
   wherein in step (5), the sequencing library is obtained by performing 1-40 PCR cycles of the PCR amplification of the DNA fragments enriched on the solid phase.

8. A method for genetic mapping of 5-methylcytosines in a target DNA, comprising the following steps:
   (1) pretreating the target DNA by extracting the target DNA and, then, using a mechanical force or a digestive enzyme, breaking the target DNA to DNA fragments having an average of 50 nucleotides to 10,000 nucleotides in length;

(2) repairing the DNA fragments and ligating the DNA fragments to a sequencing adaptor required for next generation sequencing;
(3) covalently labeling the 5-methylcytosines in the DNA fragments to which the adaptor is ligated, said labeling comprising the steps of: i) masking a naturally occurring 5-hydroxymethylcytosine in the DNA fragments to which the adaptor is ligated, such that the naturally occurring 5-hydroxymethylcytosine in the DNA fragments to which the adaptor is ligated will not be labeled in subsequent labeling steps; ii) oxidizing the 5-methylcytosines in the DNA fragments to which the adaptor is ligated to 5-hydroxymethylcytosines; iii) covalently linking an azido-group modified sugar to a hydroxymethyl group of the 5-hydroxymethylcytosines obtained from the step ii) by use of a glucosyltransferase and thereby producing an azido sugar-modified 5-hydroxymethylcytosine; and iv) reacting the azido sugar-modified 5-hydroxymethylcytosine with a click-chemistry substrate directly or indirectly linked to a biotin, thereby obtaining a labeled 5-hydroxymethylcytosine in the DNA fragments;
(4) enriching the DNA fragments having labeled 5-hydroxymethylcytosines on a solid phase by binding the DNA fragments having labeled 5-hydroxymethylcytosines to the solid phase in a binding buffer, and repeatedly washing a surface of the solid phase to remove DNA fragments that are not bound to the solid phase; and
(5) hybridizing PCR amplification primers to the sequencing adaptor to carry out a PCR amplification of the DNA fragments having labeled 5-hydroxymethylcytosines enriched on the solid phase to obtain a PCR product, and further purifying the PCR product to obtain a sequencing library for the next generation sequencing, and generating a distribution map after the next generation sequencing and mapping sequencing reads of the purified PCR product to a genome of the target DNA.

9. The method according to claim 8,
wherein said masking the naturally occurring 5-hydroxymethylcytosine in the DNA fragments to which the adaptor is ligated comprises the steps of covalently linking a sugar to a hydroxymethyl group of the 5-hydroxymethylcytosines using a glucosyltransferase, wherein the sugar is free of the azido group of the azido-group modified sugar of step iii) of the labeling steps and
said oxidizing of the 5-methylcytosines in the DNA fragments to which the adapter is ligated to 5-hydroxymethylcytosines is performed by using a ten-eleven translocation (TET) methylcytosine dioxygenase or its derivatives, analogues and recombinase.

10. The method according to claim 8,
wherein in step (1), the target DNA are derived from free DNA fragments in a body fluid, or from genomic DNA purified from tissues, cells, or organelles.

11. The method according to claim 10,
wherein the body fluid is derived from blood, urine, sweat, sputum, cerebrospinal fluid, ascites, pleural effusion, bile, or pancreatic fluid.

12. The method according to claim 8,
wherein said repairing the DNA fragments in the step (2) comprises repairing base damage in the DNA fragments, and making the 5' and 3' of the DNA fragments to blunt-ends.

13. The method according to claim 8
wherein the glucosyltransferase includes, but is not limited to, β-glucosyltransferase, α-glucosyltransferase and its derivatives, analogs or recombinant enzymes; and the azido group modified sugar includes, but is not limited to, 6-N3-glucose or another azido-modified sugar.

14. The method according to claim 8,
wherein in step (4), the solid phase comprises a magnetic ball having a diameter of 1 nm to 100 μm, agarose beads having a diameter of 1 nm to 100 μm, artificial macromolecule balls having a diameter of 1 nm to 100 μm, silicon wafers with surface modification, or biochips.

15. The method according to claim 8,
wherein in step (5), the sequencing library is obtained by performing 1-40 PCR cycles of the PCR amplification of the DNA fragments enriched on the solid phase.

\* \* \* \* \*

SEQUENCE LISTING

<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: primer

<400> SEQUENCE: 1
gatcggaaga gcacacgtct gaactccagt cacaaacatc gatctcgtat gccgtcttct    60
gcttg    65

<210> SEQ ID NO 2
<211> LENGTH: 70
<212> TYPE: DNA
<213> ORGANISM: Artificial Sequence
<220> FEATURE:
<223> OTHER INFORMATION: primer

<400> SEQUENCE: 2
aatgatacgg cgaccaccga gatctacaca tgcctaaaca ctctttccct acacgacgct    60
cttccgatct    70